US005782748A

United States Patent [19]

Palmer et al.

[11] Patent Number: 5,782,748
[45] Date of Patent: Jul. 21, 1998

[54] ENDOSCOPIC SURGICAL INSTRUMENTS HAVING DETACHABLE PROXIMAL AND DISTAL PORTIONS

[75] Inventors: Matthew A. Palmer; Saul Gottlieb, both of Miami; Nigel MacDonald, Miami Shores, all of Fla.

[73] Assignee: Symbiosis Corporation, Miami, Fla.

[21] Appl. No.: 676,614

[22] Filed: Jul. 10, 1996

[51] Int. Cl.⁶ .................................................... A61B 1/00
[52] U.S. Cl. ........................................ 600/104; 606/205
[58] Field of Search .............................. 600/104; 606/205, 606/206, 207, 208; 128/751

[56] References Cited

U.S. PATENT DOCUMENTS

| | | | |
|---|---|---|---|
| 2,113,246 | 4/1938 | Wappler | 128/321 |
| 2,790,437 | 4/1957 | Moore | 128/2 |
| 4,763,668 | 8/1988 | Macek et al. | 128/751 |
| 5,282,806 | 2/1994 | Haber et al. | 606/205 X |
| 5,419,339 | 5/1995 | Palmer | 128/751 |
| 5,454,378 | 10/1995 | Palmer et al. | 128/751 |
| 5,507,296 | 4/1996 | Bales et al. | 128/751 |
| 5,507,297 | 4/1996 | Slater et al. | 128/751 |
| 5,562,655 | 10/1996 | Mittelstadt et al. | 606/208 X |
| 5,571,137 | 11/1996 | Marlow et al. | 606/205 X |
| 5,593,402 | 1/1997 | Patrick | 606/205 X |
| 5,618,308 | 4/1997 | Holmes et al. | 606/208 X |

FOREIGN PATENT DOCUMENTS

| | | | |
|---|---|---|---|
| 225045 A1 | 10/1987 | European Pat. Off. | A61B 17/32 |
| WO 88/07839 | 10/1988 | WIPO | A61B 10/00 |

*Primary Examiner*—Beverly M. Flanagan
*Attorney, Agent, or Firm*—Finnegan, Henderson, Farabow, Garrett & Dunner, L.L.P.

[57] ABSTRACT

An endoscopic surgical instrument includes a proximal handle assembly coupled to a relatively long coil and to a relatively long pull wire extending through the long coil, and a distal jaw assembly coupled to a relatively short coil and to a relatively short pull wire extending through the short coil. The distal ends of the long coil and pull wire are provided with a first coupling device and the proximal ends of the short coil and pull wire are provided with a second coupling device which is mateable with the first coupling device. The first and second coupling devices couple the distal end of the long coil with the proximal end of the short coil and the distal end of the long pull wire with the proximal end of the short pull wire. The presently preferred pull wire coupling includes a ball and socket coupling and the presently preferred coil coupling includes a bayonet coupling. A rigid endoscopic surgical instrument with a detachable end effector assembly is also disclosed. The design of the coupling devices permits the coupling devices to be relatively small, having an overall outer diameter of two to three millimeters.

51 Claims, 6 Drawing Sheets

ENDOSCOPIC SURGICAL INSTRUMENTS HAVING DETACHABLE PROXIMAL AND DISTAL PORTIONS

This application is related to co-owned applications Ser. No. 08/310,858 filed Sep. 22, 1994 and entitled "Endoscopic Biopsy Forceps Jaws and Instruments Incorporating Same", Ser. No. 08/310,857 filed Sep. 22, 1994 and entitled "Endoscopic Biopsy Forceps Jaws and Instruments Incorporating Same", Ser. No. 08/440,326 filed May 12, 1995 entitled "Superelastic Flexible Jaws Assembly for an Endoscopic Multiple Sample Bioptome", and Ser. No. 08/412,058 filed Mar. 28, 1995 entitled "Multiple Sample Bioptome With Enhanced Biting Action", the complete disclosures of which are incorporated by reference herein. This application is also related to co-owned U.S. Pat. No. 5,507,296 entitled "Radial Jaw Biopsy Forceps", No. 5,228,451 entitled "Biopsy Forceps Device Having Stiff Distal End", No. 5,454,378 entitled "Biopsy Forceps Having Detachable Handle and Distal Jaws", and No. 5,419,339 entitled "Flexible Microsurgical Instrument Having Ground Distal Coil", the complete disclosures of which are incorporated by reference herein.

BACKGROUND OF THE INVENTION

1. Field of the Invention

This invention relates to endoscopic surgical instruments. More particularly, the present invention relates to endoscopic surgical instruments having detachable proximal and distal portions.

2. State of the Art

Endoscopic surgery is widely practiced throughout the world today and its acceptance is growing rapidly. In general, endoscopic surgery involves the use of a camera or magnifying lens inserted through a tube, while a cutter, dissector, or other surgical instrument is inserted through another tube for purposes of manipulating and/or cutting an internal organ or tissue under view of the surgeon. In endoscopic biopsy procedures, typically, the camera is located in one lumen of a flexible endoscope while the biopsy cutter is placed through another lumen thereof.

It is expected that this year more than two million endosurgical procedures will be performed which, in 1990, were performed via open surgery (MedPRO Month, I:12, p.178). The advantages of endoscopic surgery are clear in that it is less invasive, less traumatic and recovery is typically quicker. As a result, many new instruments and devices for use in endosurgery are introduced every year. Most endoscopic instruments have similar configurations with a proximal handle, an actuation mechanism, and distal end effectors coupled by a tube through which the actuation mechanism extends. (As used herein, "proximal" means closest to the surgeon and farthest from the surgical site, while "distal" means farthest from the surgeon and closest to the surgical site.) The end effectors take many forms such as grippers, cutters, forceps, dissectors and the like. Initially, rigid endoscopic surgical instruments for insertion through a trocar tube were relatively large, having an outer diameter of up to ten millimeters. More recently, rigid endoscopic instruments with outer diameters as small as two to three millimeters have been introduced.

Initially, endoscopic surgical instruments were very expensive, partly because they must be very small but still durable and reliable and the materials and manufacturing methods necessary to provide these features are expensive. Recently, however, a number of "disposable" endoscopic instruments have been introduced and their use is now widely accepted. One of the advantages of disposable endoscopic instruments over reusable instruments is that because they are used only a single time, there are no sterilization problems, (i.e., no risk of cross-contamination between patients) and no concerns about the dulling or nicking of blades or wearing of parts. However, in order to justify disposing of instruments after a single use, the instruments have to be much less expensive than the reusable tools. In order to manufacture the instruments less expensively, the disposable instruments therefore use less expensive materials. As a result, the disposable instruments are potentially less durable than the reusable instruments. It is recognized, however, that the less durable components of the disposable instruments are most often parts of the distal end effectors and that the proximal handle portion of a disposable instrument is substantially as durable as the proximal handle portion of a reusable instrument. Moreover, the distal end effectors are not so fragile that they can only withstand a single use. Despite manufacturer's recommendations to the contrary, some surgeons will sterilize disposable instruments and reuse them a few times in order to reduce "per procedure costs". Ultimately, however, it is the distal portion of the instrument which wears or breaks and mandates disposal of the entire disposable instrument.

Among the disposable endoscopic instruments in use today are a number of different types of biopsy forceps devices. These devices most often include very sharp opposing jaws for grasping and tearing tissue for biopsy. The jaws are mated with one another about a clevis pin which is mounted in a clevis. The clevis extends into a housing which is crimped to the distal end of a relatively long flexible coil. The proximal end of the coil is coupled to a handle having means for articulating the jaws. The handle generally includes a central slotted shaft about which a spool is disposed. A pull wire from the jaws extends through the coil and is attached to the spool while the coil is attached to the central shaft of the handle. Movement of the spool relative to the central shaft moves the pull wire relative to the coil and thus articulates the jaws at the distal end of the coil. In use, the jaws and coil are inserted through a flexible endoscope which is already in place in the patient's body. The surgeon guides the coil and jaws to the biopsy site while a nurse holds the handle. When the surgeon has located the jaws at the appropriate place, the nurse is instructed to operate the handle to articulate the jaws and grasp a biopsy sample. At the conclusion of the biopsy procedure, the entire forceps apparatus is either disposed of or sterilized for re-use.

The known endoscopic biopsy forceps devices of the art have the drawback that the jaws wear out long before the useful life of the handle has expired. Thus, the entire instrument must be discarded when it is only a small portion of the instrument which is inoperative.

A biopsy forceps device with detachable proximal handle and distal portions is described in U.S. Pat. No. 4,763,668 to Macek et al. It is a disadvantage of the Macek et al. detachable biopsy forceps device that attachment and detachment of the proximal and distal portions requires the screwing in and out of screws and the rotation of a sleeve which makes the attachment and detachment procedures cumbersome.

Co-owned U.S. Pat. No. 5,454,378 discloses an endoscopic biopsy forceps instrument having a handle assembly and a coil and jaws assembly. The coil and jaws assembly has a distal pair of jaws mounted on a clevis and coupled to pull wires which run through the coil to its proximal end.

The proximal ends of the coil and jaws assembly are provided with coupling devices for removably coupling the coil and pull wires to the handle assembly. The handle assembly correspondingly includes coupling devices for removably coupling the handle to the coil and to the pull wires. The handle assembly is intended to be re-usable and the coil and jaw assembly is intended to be disposable. As mentioned above, it is the forceps jaws which wear out long before the handle. However, coil and pull wire(s) also have a useful life substantially equivalent to the handle. The endoscopic biopsy forceps instrument of the '378 patent, however, requires replacement of the coil and pull wire(s) each time the jaws are replaced.

In addition to the issue of cost savings, the issue of medical waste is also important. With the advent of disposable surgical tools, the volume of medical waste materials has increased dramatically. While the biopsy forceps of the '378 patent reduce the amount of medical waste somewhat by retaining the handle, it is desirable to reduce the volume of medical waste as much as possible.

All of the known endoscopic surgical instruments which have separable proximal and distal portions provide some kind of coupling in the proximal handle. In order to greatly reduce the volume of medical waste and the cost of endoscopic procedures, it would be desirable to retain substantially all of the surgical instrument but for the end effectors. Thus far, however, the relatively minute size of the distal end of an endoscopic instrument has prohibited the provision of a separable coupling near the end effectors.

SUMMARY OF THE INVENTION

It is therefore an object of the invention to provide an endoscopic surgical instrument having separable proximal and distal portions where the separable coupling is located close to the end effectors.

It is also an object of the invention to provide an endoscopic biopsy forceps device where the distal jaws are easily separable from the proximal handle, the coil and the pull wire(s) so that the jaws may be discarded without disposing the handle, the coil, and the pull wire(s).

It is another object of the invention to provide an endoscopic biopsy forceps device where the distal jaws are easily attachable to the coil and the pull wire(s) so that the handle, the coil, and the pull wire(s) may be re-used with a new set of jaws.

It is still another object of the invention to provide an endoscopic biopsy forceps device where the distal jaws of the device attach to the coil and the pull wire(s) in substantially one step without the need for cumbersome manipulation of the device.

In accord with these objects which will be discussed in detail below, a biopsy forceps device of the present invention includes a proximal handle assembly coupled to a relatively long coil and to a relatively long pull wire extending through the long coil, and a distal jaw assembly coupled to a relatively short coil and to a relatively short pull wire extending through the short coil. The distal ends of the long coil and pull wire are provided with a first coupling means and the proximal ends of the short coil and pull wire are provided with a second coupling means which is mateable with the first coupling means. The first and second coupling means include means for coupling the distal end of the long coil with the proximal end of the short coil and means for coupling the distal end of the long pull wire with the proximal end of the short pull wire.

The presently preferred pull wire coupling means includes a ball and socket coupling and the presently preferred coil coupling means includes a bayonet coupling. With the preferred coupling means, the jaw assembly with the short coil and pull wire is coupled to the handle assembly with the long coil and pull wire by pressing the first and second coupling means together to effect mating of the ball and socket and twisting the first and second coupling means relative to each other to effect mating of the bayonet coupling. Similarly, the jaw assembly with the short coil and pull wire is uncoupled from the handle assembly with the long coil and pull wire by twisting the first and second coupling means relative to each other to effect release of the bayonet coupling and pulling apart the first and second coupling means to effect release of the ball and socket coupling.

The proximal handle assembly with the long coil and pull wire may be reused with another jaw assembly whereas the jaw assembly with the short coil and pull wire may be disposed as relatively low volume medical waste. In addition, according to the invention, different types of jaw assemblies may be provided for use with the same handle assembly, thereby allowing a practitioner to choose from a variety of jaw assemblies. For example, a double acting jaw assembly with radially arranged teeth is disclosed as well as a super elastic multiple sample jaw assembly. Either jaw assembly may be coupled to the disclosed handle assembly.

A rigid endoscopic surgical instrument with a detachable end effector assembly is also disclosed. The design of the coupling means according to the invention permits the coupling means to be relatively small, having an overall outer diameter of two to three millimeters. Moreover, the rigid handle assembly may be used with the flexible end effector assembly, if desired.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
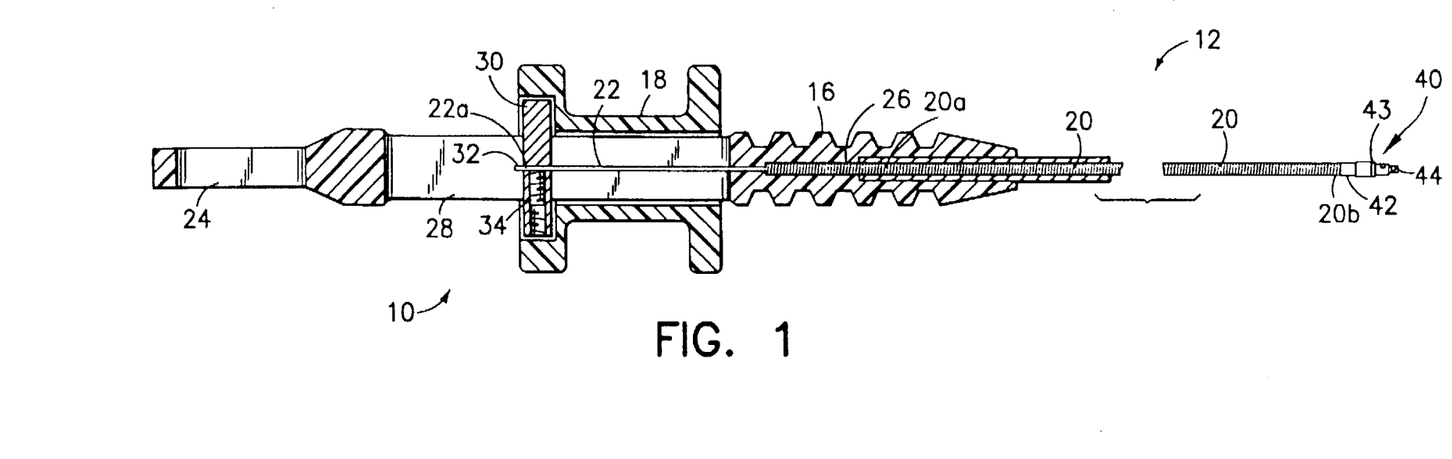
FIG. 1 is a broken side elevation view in partial section of a proximal handle assembly of an endoscopic biopsy forceps according to the invention.
Figure 2:
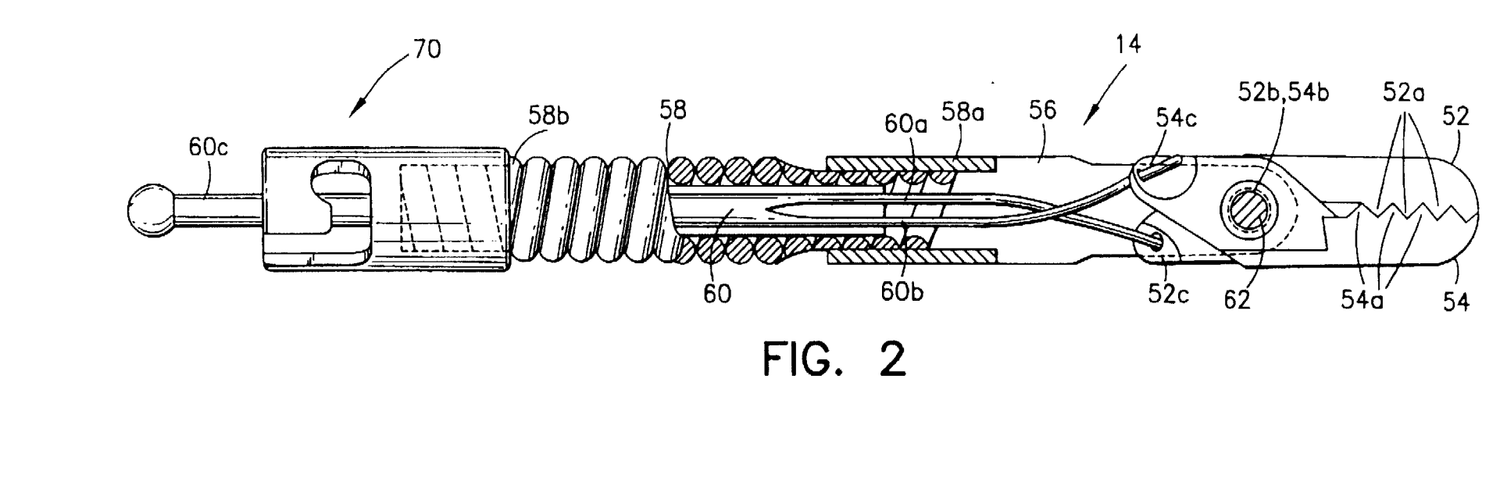
FIG. 2 is an enlarged side elevation view in partial section of a first embodiment of a distal jaw assembly of the endoscopic biopsy forceps of the invention.

Referring now to FIGS. 1 and 2, an endoscopic biopsy forceps instrument 10 according to the invention includes a proximal handle assembly 12 (FIG. 1) and a detachable distal jaw (end effector) assembly 14 (FIG. 2). The handle assembly 12 includes a central shaft 16, a displaceable spool 18, a relatively long flexible coil 20 (typically several feet in length), and a relatively long flexible pull wire 22 which extends through the coil 20. The proximal end of the shaft 16 is provided with a thumb ring 24, and a longitudinal bore 26 is provided at the distal end of the shaft 16. A longitudinal slot 28 extends from the proximal end of bore 26 to a point distal of the thumb ring 24. The proximal end 20a of the coil 20 is mounted in the bore 26. The displaceable spool 18 is provided with a cross member 30 which passes through the slot 28 in the central shaft 16. The cross member 30 is provided with a central through hole 32 and a radially engaging set screw 34. The proximal end 22a of the pull wire 22 is engaged by the set screw 34. From the foregoing, those skilled in the art will appreciate that relative movement of the shaft 16 and spool 18 results in movement of the pull wire 22 relative to the coil 20. In accord with the invention, the distal end 20b of the coil 20 and the distal end (22b in FIG. 4) of the pull wire 22 are provided with a first coupling device 40 which is described in detail below with reference to FIGS. 3 and 4.

Turning now to FIG. 2, the distal jaw assembly 14 includes a pair of jaws 52, 54, a clevis 56, a relatively short flexible coil 58 (preferably approximately eight inches or less), and a relatively short flexible pull wire 60 which extends through the coil 58. The jaws 52, 54 are preferably provided with radially arranged cutting teeth 52a, 54a, a central mounting hole 52b, 54b, and a proximal tang 52c, 54c. The jaws 52, 54 are mounted on an axle pin 62 in the clevis 56 and the clevis 56 is coupled to the distal end 58a of the coil 58 as described in any of the above-referenced co-owned patents. The distal end of the pull wire 60 is split into two filaments 60a, 60b which are respectively coupled to the tangs 52c, 54c of the jaws 52, 54 as described in any of the above-referenced co-owned patents. From the foregoing, it will be appreciated that movement of the coil 58 relative to the pull wire 60 results in opening or closing of the jaws 52, 54. In accord with the invention, the proximal end 58b of the coil 58 and the proximal end 60b of the pull wire 60 are provided with a second coupling device 70 which is described in detail below with reference to FIGS. 5 and 6 and which is mateable with the first coupling device 40 mentioned above.

Figure 3:
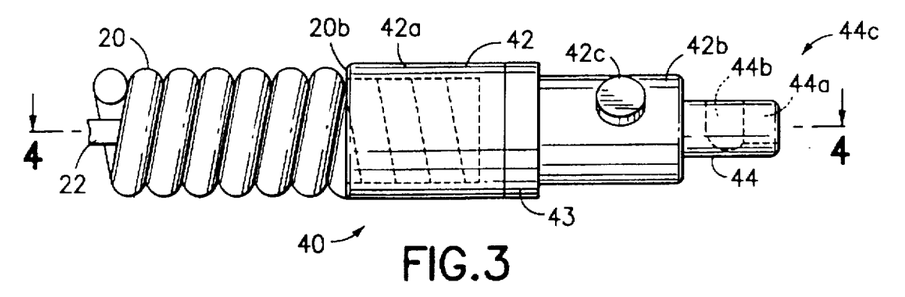
FIG. 3 is a broken enlarged side elevation view of the distal end of the handle assembly of FIG. 1.
Figure 4:
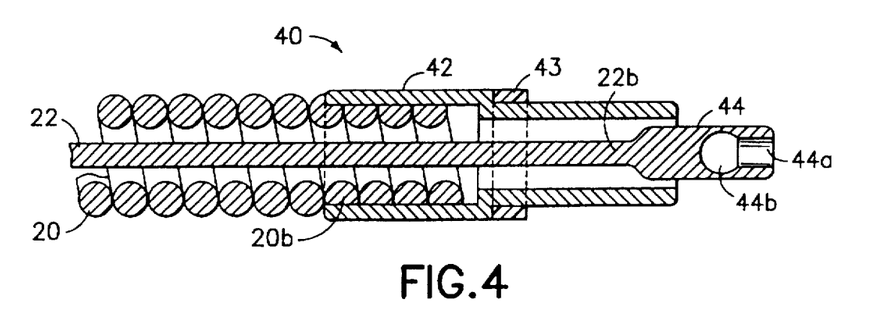
FIG. 4 is a sectional view taken along line 4—4 in FIG. 3.

Referring to FIGS. 3 and 4, the first coupling device 40 includes a male bayonet coupler 42 and a female ball-receiving socket coupler 44. The male bayonet coupler 42 is a hollow stepped cylinder (preferably formed from stainless steel) having a broad proximal portion 42a and a narrow distal portion 42b. The broad proximal portion 42a is crimped, soldered, or welded to the distal end 20b of the coil 20. The narrow distal portion 42b is provided with a radial surface protrusion 42c. An annular elastomeric washer 43 is provided on the narrow distal portion 42b abutting the broad proximal portion 42a. The ball-receiving socket coupler 44 is a cylinder (preferably formed from stainless steel) which is crimped, soldered, or welded to the distal end 22b of the pull wire 22. The coupler 44 is provided with an axial bore 44a and a radial bore 44b both of which are radially accessible as seen best in FIG. 3 and generally indicated at 44c. It will be appreciated that the outer diameter of the coupler 44 is somewhat less than the inner diameter of the narrow distal portion 42b of the bayonet coupler 42 and also somewhat smaller than the inner diameter of the coil 20. Referring FIGS. 1, 3, and 4, when the spool 18 of the handle assembly 10 is in the most distal position as shown in FIG. 1, the pull wire coupler 44 extends outside the coil coupler 42 as seen best in FIGS. 3 and 4.

Figure 5:
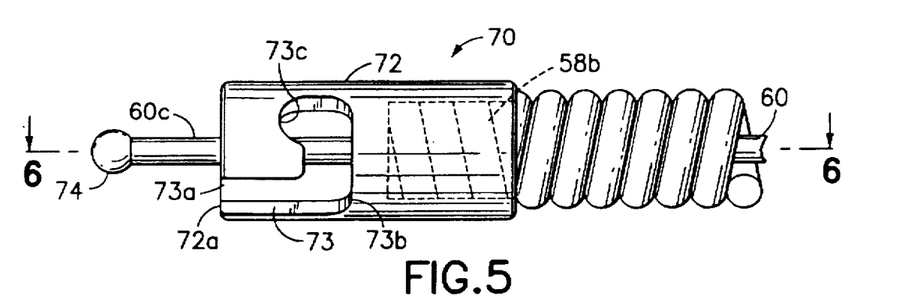
FIG. 5 is a broken enlarged side elevation view of the proximal end of the jaw assembly of FIG. 2.
Figure 6:
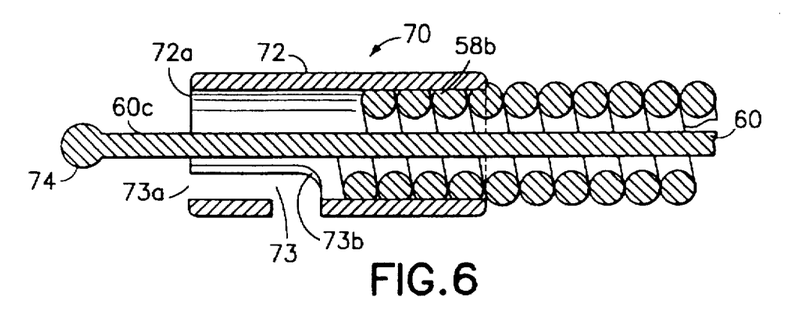
FIG. 6 is a sectional view taken along line 6—6 in FIG. 5.

Turning now to FIGS. 5 and 6, the second coupling device 70 includes a female bayonet coupler 72 and a male socket-engaging ball coupler 74. The female bayonet coupler 72 is a substantially cylindrical (preferably stainless steel) member having a substantially L-shaped cut-out 73 extending distally from its proximal end 72a. As seen best in FIG. 5, the cut-out 73 has a proximal entrance 73a, a central bend 73b and a locking seat 73c. The distal end 72b of the female bayonet coupler 72 is crimped, soldered, or welded to the ground proximal end 58b of the short coil 58. The male ball coupler 74 is a substantially spherical member at the proximal end 60c of the pull wire 60. According to a presently preferred embodiment, the ball coupler 74 is formed by heating the proximal end 60c of the pull wire 60 until it melts and forms an integral sphere 74.

Figure 7:
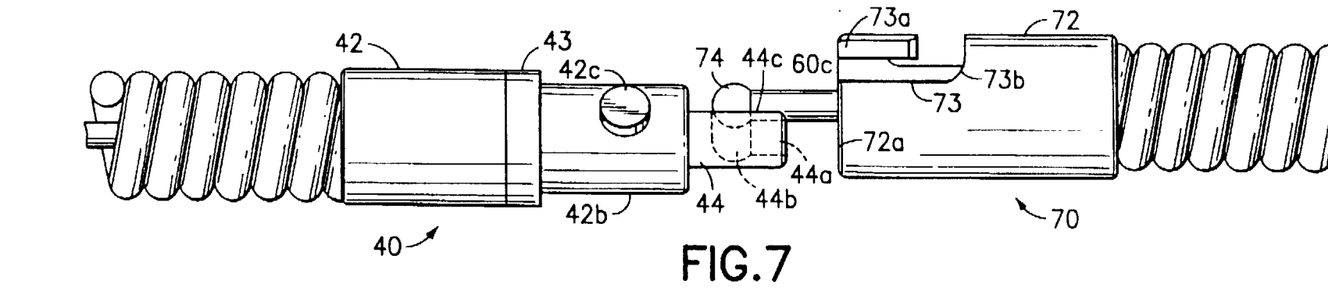
FIG. 7 is a broken enlarged side elevation view of the distal end of the handle assembly of FIG. 1 and the proximal end of the jaw assembly of FIG. 2 in a first stage of coupling.
Figure 8:
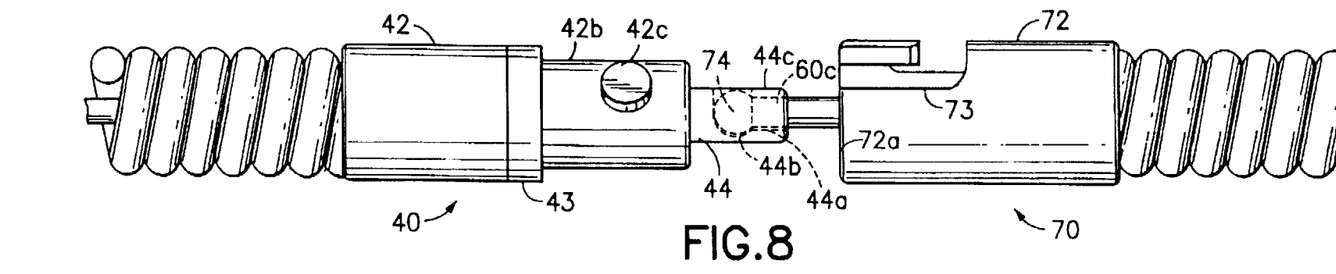
FIG. 8 is a broken enlarged side elevation view of the distal end of the handle assembly of FIG. 1 and the proximal end of the jaw assembly of FIG. 2 in a second stage of coupling.
Figure 9:
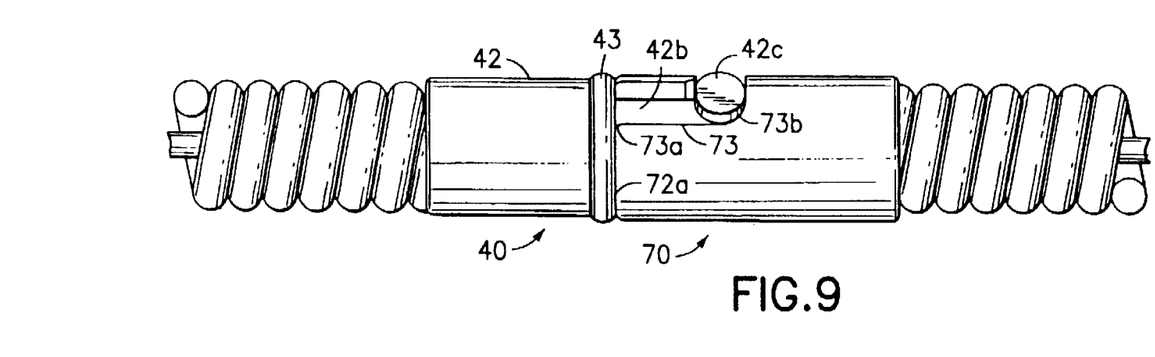
FIG. 9 is a broken enlarged side elevation view of the distal end of the handle assembly of FIG. 1 and the proximal end of the jaw assembly of FIG. 2 in a third stage of coupling.
Figure 10:
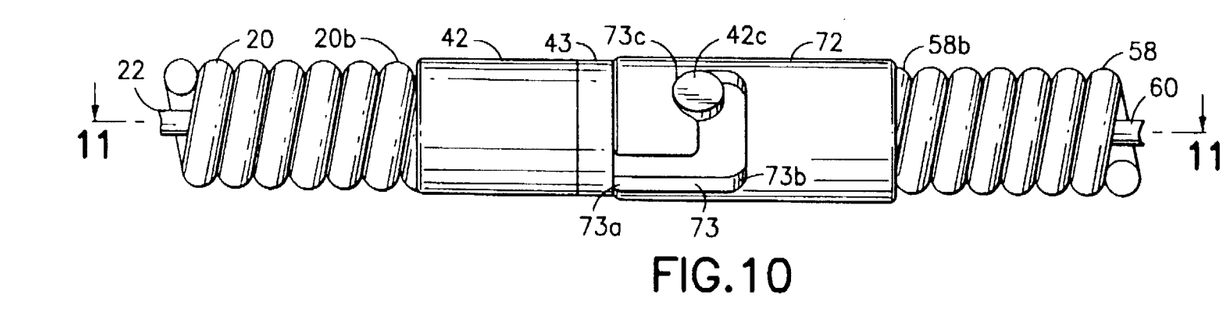
FIG. 10 is a broken enlarged side elevation view of the distal end of the handle assembly of FIG. 1 coupled to the proximal end of the jaw assembly of FIG. 2.
Figure 11:
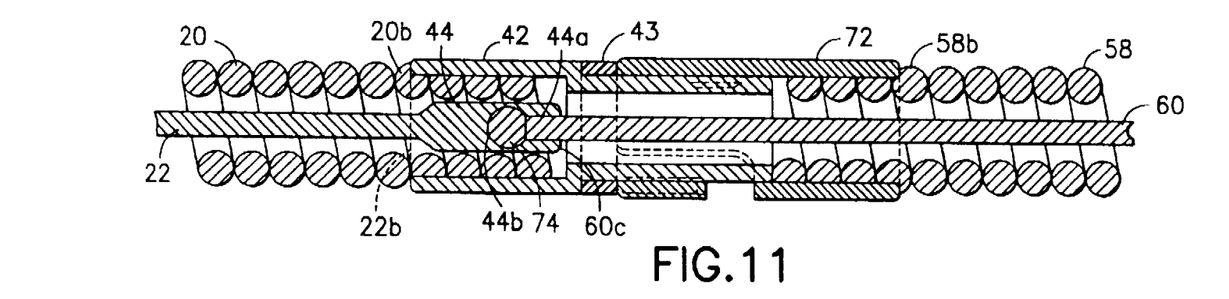
FIG. 11 is a sectional view taken along line 11—11 of FIG. 10.
Figure 12:
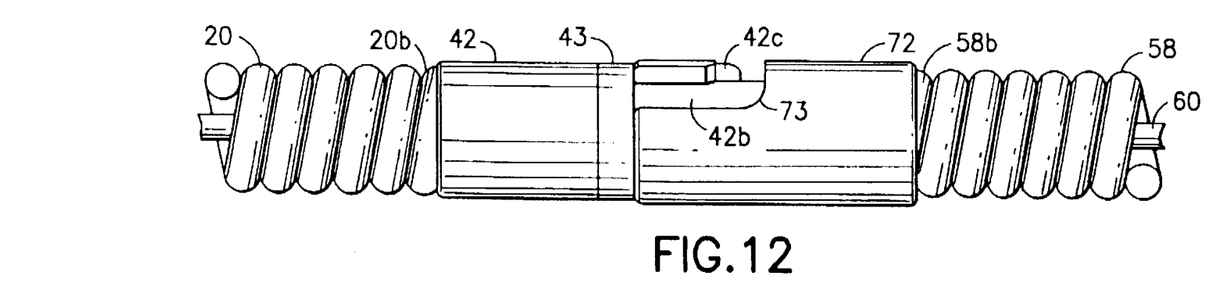
FIG. 12 is a broken enlarged bottom view of the distal end of the handle assembly of FIG. 1 coupled to the proximal end of the jaw assembly of FIG. 2.

From the foregoing, those skilled in the art may readily appreciate how the first coupling device 40 is coupled with the second coupling device 70 as shown in FIGS. 7 through 12. In order to couple the first and second coupling devices, the ball coupler 74 is placed in the socket coupler 44 via the radial access 44c as shown in FIGS. 7 and 8. The coupling devices 40, 70 are then moved toward each other and the entrance 73a to the cut-out 73 on the coupler 72 is aligned with the protrusion 42c on the coupler 42 so that the radial protrusion 42c may enter the cut-out 73 as shown in FIG. 9. The proximal end 72a of the coupler 72 is pressed against the resilient washer 43 and compresses it in order to locate the radial protrusion 42c at the bend 73b in the cut-out 73 as shown in FIG. 9. The couplers 42 and 72 are then rotated relative to each other to move the protrusion 42c into the locking seat 73c of the cut-out 73 as shown in FIG. 10. It will be appreciated that the resilient washer 43 urges the couplers 42, 72 apart from each other and thereby helps to hold the protrusion 42c in the locking seat 73c of the cut-out 73. As seen best in FIG. 11, the relative dimensions of the socket coupler 44, the ball coupler 74, the interior lumen of the coil 20, and the interior lumen of the distal portion 42b of the bayonet coupler 42, prohibit the ball coupler 74 from exiting the socket coupler 44 when the couplers 40 and 70 are joined together. Uncoupling the couplers 40 and 70 is effected by reversing the steps described, i.e. by pressing the couplers together, rotating them to move the protrusion out of the locking seat, separating the couplers 42, 72 and lifting the ball coupler 74 out of the socket coupler 44. As mentioned above, the frictional surface 72c on the coupler 72 aids the practitioner in rotating it relative to the coupler 42.

As mentioned above, the distal jaw assembly may be removed from the proximal handle assembly and discarded after use. The handle assembly with the longer coil and pull wire may be reused (preferably after sterilization) with another jaw assembly, thereby minimizing the cost of a procedure and the volume of medical waste. Moreover, a single handle assembly may be used with different types of jaw assemblies or end effectors.

Those skilled in the art will appreciate that the jaw assembly 14 described above with reference to FIG. 2 is adequate to obtain a single biopsy sample. However, other types of jaw assemblies may be provided for use with the handle assembly 12 described above with reference to FIG. 1.

Figure 13:
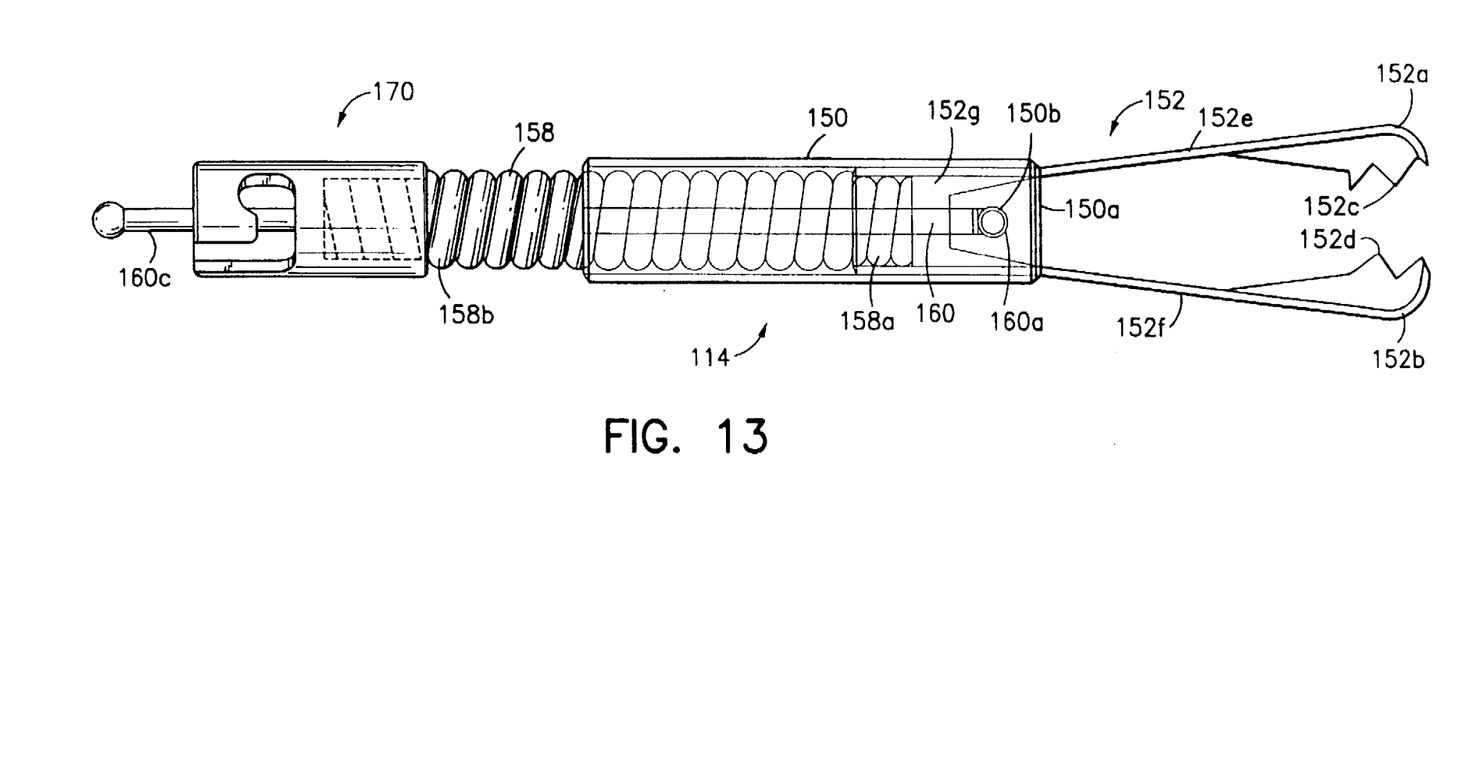
FIG. 13 is a view similar to FIG. 2 of a second embodiment of a distal jaw assembly of the endoscopic biopsy forceps of the invention.

Turning now to FIG. 13, a multiple sample jaw bioptome 114 includes a relatively short coil 158 which is substantially the same as the coil 58 described above, a relatively short pull wire 160 which extends through the coil 158, a cylindrical sleeve 150 having a distal edge 150a, and a jaw assembly 152. The jaw assembly 152 includes a pair of opposed jaw cups 152a, 152b each preferably having a plurality of sharp teeth 152c, 152d. A resilient, preferably narrow, arm 152e, 152f extends proximally from each jaw cup 152a, 152b. A cylindrical base member 152g joins the proximal ends of the arms 152e, 152f. The narrow resilient arms 152e, 152f are biased apart from each other, thereby urging the jaw cups 152a, 152b apart. The cylindrical base member 152g of the jaw assembly 152 is mechanically coupled to the distal end 158a of the coil 158. The cylindrical sleeve 150 is coupled to the distal end 160a of the pull wire 160 by providing the sleeve 150 with a lateral hole 150b and providing the distal end 160a of the pull wire with a substantially right angle bend. The distal end 160a of the pull wire 160 is soldered or otherwise mechanically attached in the hole 150b in the sleeve 150. Those skilled in the art will appreciate that distal movement of the pull wire 160 relative to the coil 158 will move the cylinder 150 over the arms 152e, 152f to thereby close the jaw cups 152a, 152b. Similarly, proximal movement the pull wire 160 relative to the coil 158 and will move the cylinder 150 back from the arms 152e, 152f to thereby open the jaw cups 152a, 152b. According to the invention, the proximal end 160c of the pull wire and the proximal end of the coil 158b are coupled to a coupling device 170 which is substantially the same as the coupling device 70 described above. It will therefore be understood that the multiple sample bioptome 114 shown in FIG. 13 may be attached to the handle assembly 12 shown in FIG. 1 by following the steps described above with reference to FIGS. 7–12.

Figures 14, 15:
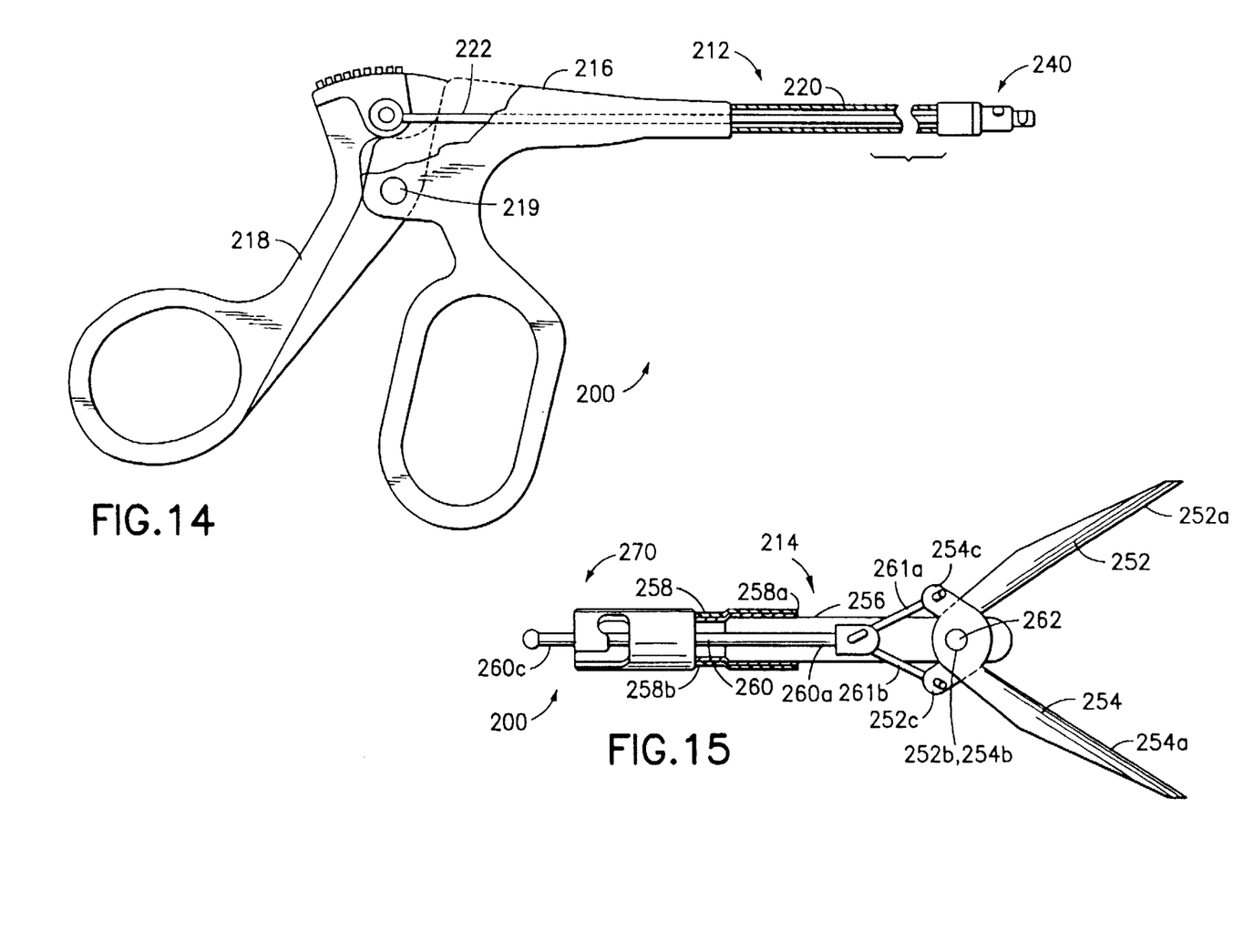
FIG. 14 is a broken side elevation view in partial section of a proximal handle assembly of a rigid endoscopic surgical instrument according to the invention.
FIG. 15 is a side elevation view in partial section of an end effector assembly of the rigid endoscopic surgical instrument of the invention.

Thus far the invention has been described with reference to flexible microsurgical instruments, i.e. those having flexible coils coupling the handle to the end effectors. The invention may also be used, however, with microsurgical instruments having a rigid tube in lieu of a flexible coil. Turning now to FIGS. 14 and 15, an endoscopic instrument 200 according to the invention includes a proximal handle assembly 212 and a distal end effector assembly 214. The handle assembly 212 includes a stationary portion 216 and a movable lever portion 218 which is pivotally attached to the stationary portion by an axle 219. A relatively rigid tube 220 is coupled to the stationary portion 216 and extends distally therefrom. A relatively rigid push rod 222 is coupled to the lever portion 218 and extends through the tube 220. Movement of the lever portion 218 relative to the stationary portion 216 results in movement of the push rod 222 through the tube 220. The distal ends of the tube 220 and the push rod 222 are coupled to a coupling device 240 which is substantially the same as the coupling device 40 described above.

The end effector assembly 214 of instrument 200 includes a relatively short tube 258 with a relatively short push rod 260 extending therethrough. A clevis 256 is coupled to the distal end 258a of the tube 250 (or alternatively is formed integral therewith) and a pair of end effectors 252, 254 are mounted in the clevis 256 on an axle pin 262. More particularly, each end effector 252, 254 has a distal working surface 252a, 254a, a central mounting hole 252b, 254b, and a proximal tang 2252c, 254c. The distal working surface may be a gripping surface or a cutting surface, for example. The end effectors are mounted on the axle pin 262 via their mounting hole 252b, 254b. The tangs 252c, 254c of the end effectors are coupled to the distal end 260a of the push rod 260 via links 261a, 261b.

It will be appreciated that movement of the push rod 260 through the tube 258 will open and close the end effectors. According to the invention, the proximal end 258b of the tube 258 and the proximal end 260c of the push rod 260 are coupled to a coupling device 270 which is substantially the same as the coupling device 70 described above. Moreover, it will be appreciated that the handle assembly 212 and the end effector assembly 214 may be coupled to each other by following the steps described above with reference to FIGS. 7–12.

There have been described and illustrated herein several embodiments of an endoscopic surgical instrument having separable proximal and distal portions. While particular embodiments of the invention have been described, it is not intended that the invention be limited thereto, as it is intended that the invention be as broad in scope as the art will allow and that the specification be read likewise. Thus, while particular members have been disclosed as being male and female, it will be appreciated that male and female members could be interchanged. For example, the distal portion of the instrument has been shown with a male ball coupling and a female bayonet coupling whereas the proximal portion of the instrument has been shown with male bayonet coupling and a female socket coupling. It will be appreciated that four possible permutations of arranging these couplings are possible. Also, while the bayonet couplings have been shown using a single radial projection and a single bayonet slot, a pair of projections and slots could be used. It will also be understood that any of the end effector assemblies 14, 114, 214 may be used with either of the handle assemblies 12, 212. It will therefore be appreciated by those skilled in the art that yet other modifications could be made to the provided invention without deviating from its spirit and scope as so claimed.

We claim:

1. An endoscopic surgical instrument, comprising:

a first tubular member having a proximal end and a distal end;

a first control member having a proximal end and a distal end and extending through said first tubular member;

a proximal actuation means coupled to said proximal ends of said first tubular member and said first control member for imparting movement to one of said first tubular member and said first control member relative to the other;

a second tubular member having a proximal end and a distal end;

a second control member having a proximal end and a distal end and extending through said second tubular member;

a pair of end effectors coupled to said distal end of said second tubular member, at least a first of said pair of end effectors being coupled to said distal end of said second control member such that movement of said second control member relative to said second tubular member moves said at least first of said pair of end effectors relative to a second of said pair of end effectors;

first coupling means protruding from and coupled to said distal ends of said first tubular member and said first control member for removably coupling said proximal actuation means to said pair of end effectors; and second coupling means coupled to said proximal ends of second tubular member and said second control member for mating with said first coupling means to removably couple said proximal actuation means to said pair of end effectors.

2. An endoscopic surgical instrument according to claim 1, wherein:
said first coupling means includes a first bayonet coupler and one of a ball and socket coupler.

3. An endoscopic surgical instrument according to claim 2, wherein:
said second coupling means includes a second bayonet coupler and the other of a ball and socket coupler.

4. An endoscopic surgical instrument according to claim 3, wherein:
said first bayonet coupler is one of a male and a female bayonet coupler and said second bayonet coupler is the other of a male and a female bayonet coupler.

5. An endoscopic surgical instrument according to claim 4, wherein: said male bayonet coupler includes a resilient member for biasing said male bayonet coupler.

6. An endoscopic surgical instrument according to claim 1, wherein:
said first coupling means and said second coupling means each have an outer diameter no larger than approximately five millimeters.

7. An endoscopic surgical instrument according to claim 1, wherein:
said first tubular member is a relatively long rigid tube and said second tubular member is a relatively short rigid tube.

8. An endoscopic surgical instrument according to claim 1, wherein:
said pair of end effectors are biopsy forceps.

9. An endoscopic surgical instrument according to claim 1, wherein:
said pair of end effectors are a pair of grippers.

10. An endoscopic surgical instrument of claim 1, wherein said first coupling means permanently protrudes from said distal end of said first tubular member.

11. An endoscopic surgical instrument, comprising:
a first tubular member having a proximal end and a distal end;
a first control member having a proximal end and a distal end and extending through said first tubular member;
a proximal actuation means coupled to said proximal ends of said first tubular member and said first control member for imparting movement to one of said first tubular member and said first control member relative to the other;
a second tubular member having a proximal end and a distal end;
a second control member having a proximal end and a distal end and extending through said second tubular member;
a pair of end effectors coupled to said distal end of said second tubular member, at least a first of said pair of end effectors being coupled to said distal end of said second control member such that movement of said second control member relative to said second tubular member moves said at least first of said pair of end effectors relative to a second of said pair of end effectors;

first coupling means coupled to said distal ends of said first tubular member and said first control member for removably coupling said proximal actuation means to said pair of end effectors; and second coupling means coupled to said proximal ends of second tubular member and said second control member for mating with said first coupling means to removably couple said proximal actuation means to said pair of end effectors, wherein said first tubular member is a relatively long flexible coil and said second tubular member is a relatively short flexible coil.

12. An endoscopic surgical instrument according to claim 11, wherein:
said relatively long flexible coil is several feet long and said relatively short flexible coil is less than one foot long.

13. An endoscopic surgical instrument according to claim 11, wherein:
said relatively long flexible coil and said relatively short flexible coil have substantially identical outer diameters of approximately two to five millimeters.

14. An endoscopic instrument handle assembly for use with a detachable end effector assembly having
a first tubular member with a proximal end and a distal end,
a first control member with a proximal end and a distal end and extending through the first tubular member,
a pair of end effectors coupled to the distal end of the first tubular member, at least one of the pair of end effectors being coupled to the distal end of first control member such that movement of the first control member relative to the first tubular member moves the at least one of the pair of end effectors relative to other of the pair of end effectors, and
first coupling means coupled to the proximal ends of the first tubular member and the first control member for coupling the end effector assembly to said handle assembly, said handle assembly comprising:
a second tubular member having a proximal end and a distal end;
a second control member having a proximal end and a distal end and extending through said second tubular member;
a proximal actuation means coupled to said proximal ends of said second tubular member and said second control member for imparting movement to one of said second tubular member and said second control member relative to each other; and
second coupling means protruding from and coupled to said distal ends of said second tubular member and said second control member for mating with said first coupling means to removably couple said proximal actuation means to said pair of end effectors.

15. A handle assembly according to claim 14, wherein:
said second coupling means includes a bayonet coupler and one of a ball and socket coupler.

16. A handle assembly according to claim 15, wherein:
said bayonet coupler includes a resilient member.

17. An end effector assembly according to claim 16, wherein:
said pair of end effectors are a pair of grippers.

18. A handle assembly according to claim 14, wherein:
said second tubular member is a rigid tube.

19. An endoscopic instrument handle assembly of claim 14, wherein said second coupling means permanently protrudes from said distal end of said second tubular member.

20. An endoscopic instrument handle assembly for use with a detachable end effector assembly having
a first tubular member with a proximal end and a distal end,
a first control member with a proximal end and a distal end and extending through the first tubular member,
a pair of end effectors coupled to the distal end of the first tubular member, at least one of the pair of end effectors being coupled to the distal end of first control member such that movement of the first control member relative to the first tubular member moves the at least one of the pair of end effectors relative to other of the pair of end effectors, and
first coupling means coupled to the proximal ends of the first tubular member and the first control member for coupling the end effector assembly to said handle assembly,
said handle assembly comprising:
a second tubular member having a proximal end and a distal end;
a second control member having a proximal end and a distal end and extending through said second tubular member;
a proximal actuation means coupled to said proximal ends of said second tubular member and said second control member for imparting movement to one of said second tubular member and said second control member relative to each other; and
second coupling means coupled to said distal ends of said second tubular member and said second control member for mating with said first coupling means to removably couple said proximal actuation means to said pair of end effectors,
wherein said second tubular member is a relatively long flexible coil.

21. A handle assembly according to claim 20, wherein:
said relatively long flexible coil has an outer diameter of approximately two to five millimeters.

22. An endoscopic surgical end effector assembly for use with a detachable handle assembly having
a first tubular member having a proximal end and a distal end,
a first control member having a proximal end and a distal end and extending through the first tubular member,
a proximal actuation means coupled to the proximal ends of the first tubular member and the first control member for imparting relative movement to one of the first tubular member and the first control member, and
first coupling means protruding from and coupled to the distal ends of the first tubular member and the first control member for removably coupling the proximal actuation means to said end effector assembly, said end effector assembly comprising:
a second tubular member having a proximal end and a distal end;
a second control member having a proximal end and a distal end and extending through said second tubular member;
a pair of end effectors coupled to said distal end of said second tubular member, at least one of said pair of end effectors being coupled to said distal end of said second control member such that movement of said second control member relative to said second tubular member moves said at least one of said pair of end effectors relative to the other of said pair of end effectors; and
second coupling means coupled to said proximal ends of second tubular member and said second control member for fixed connection with the first coupling means external to the first tubular member to removably couple the proximal actuation means to said pair of end effectors.

23. An end effector assembly according to claim 22, wherein:
said second coupling means includes a bayonet coupler and one of a ball and socket coupler.

24. An end effector assembly according to claim 22, wherein:
said second tubular member is a relatively short rigid tube.

25. An end effector assembly according to claim 22, wherein:
said pair of end effectors are biopsy forceps.

26. An endoscopic instrument end effector assembly of claim 22, wherein said first coupling means permanently protrudes from the distal end of the first tubular member, and said fixed connection between said first and second coupling means is permanently external to the first tubular member.

27. An endoscopic surgical end effector assembly for use with a detachable handle assembly having
a first tubular member having a proximal end and a distal end,
a first control member having a proximal end and a distal end and extending through the first tubular member,
a proximal actuation means coupled to the proximal ends of the first tubular member and the first control member for imparting relative movement to one of the first tubular member and the first control member, and
first coupling means coupled to the distal ends of the first tubular member and the first control member for removably coupling the proximal actuation means to said end effector assembly, said end effector assembly comprising:
a second tubular member having a proximal end and a distal end;
a second control member having a proximal end and a distal end and extending through said second tubular member;
a pair of end effectors coupled to said distal end of said second tubular member, at least one of said pair of end effectors being coupled to said distal end of said second control member such that movement of said second control member relative to said second tubular member moves said at least one of said pair of end effectors relative to the other of said pair of end effectors; and
second coupling means coupled to said proximal ends of second tubular member and said second control member for mating with the first coupling means to removably couple the proximal actuation means to said pair of end effectors, wherein said second tubular member is a relatively short flexible coil.

28. An end effector assembly according to claim 27, wherein:
said relatively short flexible coil has an outer diameter of approximately two to five millimeters.

29. An endoscopic surgical instrument, comprising:
a relatively long flexible tubular member having proximal and distal ends;
a control member having proximal and distal ends and extending through said long flexible tubular member;
a proximal actuator coupled to said proximal ends of said long flexible tubular member and said control member for imparting movement of said long flexible tubular member relative to said control member;
a first connection device coupled to said distal ends of said long flexible tubular member and said control member; and
a detachable distal assembly having end effectors and a second connection device removably coupled to said first connection device so that said proximal actuator actuates said end effectors.

30. An endoscopic surgical instrument of claim 29, wherein said first connection device protrudes from said distal end of said long flexible tubular member.

31. An endoscopic surgical instrument of claim 29, wherein said detachable distal assembly includes a relatively short flexible tubular member having proximal and distal ends, and a second control member having proximal and distal ends and extending through said short flexible tubular member, wherein said second connection device is coupled to said proximal ends of said short flexible tubular member and said second control member.

32. An endoscopic surgical instrument of claim 31, wherein said end effectors are coupled to said distal ends of said short flexible tubular member and said second control member.

33. An endoscopic surgical instrument of claim 31, wherein said long flexible tubular member is a coil and said short flexible tubular member is a coil.

34. An endoscopic surgical instrument of claim 33, wherein said long coil is several feet long and said short coil is less than one foot long.

35. An endoscopic surgical instrument of claim 29, wherein said first connection device includes a first bayonet coupler and one of a ball and socket coupler.

36. An endoscopic surgical instrument of claim 35, wherein said second connection device includes a second bayonet coupler and the other of a ball and socket coupler.

37. An endoscopic surgical instrument of claim 36, wherein said first bayonet coupler is one of a male and a female bayonet coupler and said second bayonet coupler is the other of a male and a female bayonet coupler.

38. An endoscopic surgical instrument of claim 37, wherein said male bayonet coupler includes a resilient member for biasing said male bayonet coupler.

39. An endoscopic surgical instrument of claim 29, wherein said end effectors are biopsy forceps.

40. An endoscopic surgical instrument of claim 29, wherein said end effectors are a pair of grippers.

41. An endoscopic instrument handle assembly for use with a detachable distal end assembly having a first connection device and end effectors, said handle assembly comprising:
a relatively long flexible tubular member having proximal and distal ends;
a control member having proximal and distal ends and extending through said long flexible tubular member;
a proximal actuator coupled to said proximal ends of said long flexible tubular member and said control member for imparting movement of said long flexible tubular member relative to said control member; and
a second connection device coupled to said distal ends of said long flexible tubular member and said control member for connection with the first connection device so that said proximal actuator actuates the end effectors.

42. A handle assembly of claim 41, wherein said second connection device protrudes from said distal end of said long flexible tubular member.

43. A handle assembly of claim 42, wherein said second connection device permanently protrudes from said distal end of said long flexible tubular member.

44. A handle assembly of claim 41, wherein said second connection device includes a bayonet coupler and one of a ball and socket coupler.

45. A handle assembly of claim 44, wherein said bayonet coupler includes a resilient member.

46. A handle assembly of claim 41, wherein said long flexible tubular member is a coil.

47. An endoscopic instrument distal end assembly for use with a detachable handle assembly having a first connection device and a proximal actuator, said distal end assembly comprising:
a relatively short flexible tubular member having proximal and distal ends;
a control member having proximal and distal ends and extending through said short flexible tubular member;
end effectors coupled to said distal ends of said short flexible tubular member and said control member; and
a second connection device coupled to said proximal ends of said short flexible tubular member and said control member for connection with the first connection device so that the proximal actuator actuates said end effectors.

48. A distal end assembly of claim 47, wherein said second connection device includes a bayonet couple and one of a ball and socket coupler.

49. A distal end assembly of claim 47, wherein said short flexible tubular member is a coil.

50. A distal end assembly of claim 47, wherein said end effectors are biopsy forceps.

51. A distal end assembly of claim 47, wherein said end effectors are a pair of grippers.

* * * * *